(12) United States Patent
Peterson et al.

(10) Patent No.: US 11,771,554 B2
(45) Date of Patent: Oct. 3, 2023

(54) SUPRA ANNULAR TAPERED BALLOON EXPANDABLE STENT FOR TRANSCATHETER IMPLANTATION OF A CARDIAC VALVE PROSTHESIS

(71) Applicant: Medtronic, Inc., Minneapolis, MN (US)

(72) Inventors: Justin Peterson, Santa Rosa, CA (US); Tracey Tien, Tustin, CA (US); Michael Krivoruchko, Forestville, CA (US); Yas Neuberger, Santa Rosa, CA (US); Stuart Kari, Windsor, CA (US); Justin Goshgarian, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 1 day.

(21) Appl. No.: 15/931,708

(22) Filed: May 14, 2020

(65) Prior Publication Data

US 2020/0360134 A1 Nov. 19, 2020

Related U.S. Application Data

(60) Provisional application No. 62/849,208, filed on May 17, 2019.

(51) Int. Cl.
*A61F 2/24* (2006.01)
*A61F 2/90* (2013.01)
*A61F 2/82* (2013.01)

(52) U.S. Cl.
CPC .......... *A61F 2/2418* (2013.01); *A61F 2/2433* (2013.01); *A61F 2/90* (2013.01);
(Continued)

(58) Field of Classification Search
CPC ........ A61F 2/2418; A61F 2/90; A61F 2/2433; A61F 2002/825; A61F 2230/0054;
(Continued)

(56) References Cited

U.S. PATENT DOCUMENTS 5,330,500 A 7/1994 Song
5,411,552 A 5/1995 Andersen et al.
(Continued)

FOREIGN PATENT DOCUMENTS

WO 2003011195 A2 2/2003
WO 20060127765 A1 11/2006
(Continued)

*Primary Examiner* — Megan Y Wolf
(74) *Attorney, Agent, or Firm* — MEDLER FERRO WOODHOUSE & MILLS PLLC

(57) ABSTRACT

A transcatheter valve prosthesis includes a stent and a prosthetic valve disposed within the stent. The stent is balloon expandable and includes an inflow portion, an outflow portion, and a transition portion extending between the inflow portion and the outflow portion. A diameter of an inflow end of the transcatheter valve prosthesis is greater than a diameter of an outflow end of the transcatheter valve prosthesis. The transcatheter valve prosthesis has a tapered profile along an entire height thereof when in the stent is in the expanded configuration. The inflow end of the transcatheter valve prosthesis is configured to sit within and contact an aortic annulus of the native aortic valve and the outflow end of the transcatheter valve prosthesis being configured to float within an ascending aorta without contacting the ascending aorta due to the tapered profile of the transcatheter valve prosthesis.

18 Claims, 11 Drawing Sheets

(52) U.S. Cl.
CPC . *A61F 2002/825* (2013.01); *A61F 2230/0054* (2013.01); *A61F 2230/0067* (2013.01); *A61F 2250/0039* (2013.01)

(58) Field of Classification Search
CPC ...... A61F 2230/0067; A61F 2250/0039; A61F 2250/0023; A61F 2250/0014
See application file for complete search history.

(56) References Cited

U.S. PATENT DOCUMENTS

| | | | |
|---|---|---|---|
| 5,840,081 A | 11/1998 | Andersen et al. | |
| 5,931,969 A | 8/1999 | Carpentier et al. | |
| 6,168,614 B1 | 1/2001 | Andersen et al. | |
| 6,210,957 B1 | 4/2001 | Carpentier et al. | |
| 6,214,054 B1 | 4/2001 | Cunanan et al. | |
| 6,458,153 B1 | 10/2002 | Bailey et al. | |
| 6,547,827 B2 | 4/2003 | Carpentier et al. | |
| 6,561,970 B1 | 5/2003 | Carpentier et al. | |
| 6,582,462 B1 | 6/2003 | Andersen et al. | |
| 6,730,118 B2 | 5/2004 | Spenser et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,198,646 B2 | 4/2007 | Figulia et al. | |
| 7,201,772 B2 | 4/2007 | Schwammenthal et al. | |
| 7,214,344 B2 | 5/2007 | Carpentier et al. | |
| 7,252,682 B2 | 8/2007 | Seguin | |
| 7,329,278 B2 | 2/2008 | Seguin et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| RE40,570 E | 11/2008 | Carpentier et al. | |
| 7,470,285 B2 | 12/2008 | Nugent et al. | |
| 7,510,575 B2 | 3/2009 | Spenser et al. | |
| 7,530,253 B2 | 5/2009 | Spenser et al. | |
| 7,585,321 B2 | 9/2009 | Cribier | |
| 7,618,446 B2 | 11/2009 | Andersen et al. | |
| 7,682,390 B2 * | 3/2010 | Seguin | A61F 2/2433 623/2.14 |
| 7,780,723 B2 | 8/2010 | Taylor | |
| 7,780,726 B2 | 8/2010 | Seguin | |
| 7,789,909 B2 | 9/2010 | Andersen et al. | |
| 7,846,203 B2 | 12/2010 | Cribier | |
| 7,993,394 B2 | 8/2011 | Hariton et al. | |
| 8,163,011 B2 | 4/2012 | Rankin | |
| 8,236,045 B2 | 8/2012 | Benichou et al. | |
| 8,579,966 B2 * | 11/2013 | Seguin | A61F 2/2418 623/2.18 |
| 8,926,694 B2 * | 1/2015 | Costello | A61F 2/2436 623/2.11 |
| 9,089,422 B2 | 7/2015 | Ryan et al. | |
| 9,901,447 B2 | 2/2018 | Braido et al. | |
| 9,943,407 B2 | 4/2018 | Tuval et al. | |
| 10,058,420 B2 | 8/2018 | Levi | |
| 2006/0178740 A1 | 8/2006 | Stacchino et al. | |
| 2006/0259137 A1 | 11/2006 | Artof et al. | |
| 2007/0078510 A1 | 4/2007 | Ryan | |
| 2007/0270944 A1 | 11/2007 | Bergheim et al. | |
| 2008/0154355 A1 | 6/2008 | Benichou et al. | |
| 2009/0192591 A1 | 7/2009 | Ryan et al. | |
| 2010/0268332 A1 | 10/2010 | Tuval et al. | |
| 2011/0015729 A1 | 1/2011 | Jimenez et al. | |
| 2011/0166636 A1 | 7/2011 | Rowe | |
| 2011/0264196 A1 * | 10/2011 | Savage | A61F 2/2418 623/2.11 |
| 2011/0301700 A1 | 12/2011 | Fish et al. | |
| 2011/0313515 A1 | 12/2011 | Quadri et al. | |
| 2012/0053681 A1 | 3/2012 | Alkhatib et al. | |
| 2012/0071969 A1 | 3/2012 | Li et al. | |
| 2012/0078356 A1 | 3/2012 | Fish et al. | |
| 2013/0023984 A1 | 1/2013 | Conklin | |
| 2013/0150956 A1 * | 6/2013 | Yohanan | A61F 2/2409 623/2.14 |
| 2013/0184811 A1 | 7/2013 | Rowe et al. | |
| 2014/0277389 A1 | 9/2014 | Braido et al. | |
| 2014/0330371 A1 * | 11/2014 | Gloss | A61F 2/07 623/2.17 |
| 2015/0018944 A1 | 1/2015 | O'Connell et al. | |
| 2019/0091014 A1 * | 3/2019 | Arcaro | A61F 2/24 |
| 2020/0078167 A1 * | 3/2020 | Quijano | A61F 2/2418 |
| 2022/0160502 A1 * | 5/2022 | Jin | A61F 2/90 |

FOREIGN PATENT DOCUMENTS

| | | |
|---|---|---|
| WO | 2008150529 A1 | 12/2008 |
| WO | 2012032187 A1 | 3/2012 |

* cited by examiner

SUPRA ANNULAR TAPERED BALLOON EXPANDABLE STENT FOR TRANSCATHETER IMPLANTATION OF A CARDIAC VALVE PROSTHESIS

CROSS-REFERENCE TO RELATED APPLICATIONS

This application claims the benefit of U.S. Provisional Patent Application Ser. No. 62/849,208, filed May 17, 2019, which is hereby incorporated by reference in its entirety for all purposes.

FIELD OF THE INVENTION

The present invention relates to transcatheter valve prostheses that are radially expandable by a balloon.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place.

When designing a prosthetic valve, valve-stent integration and stent mechanical performance often have competing needs or requirements. For example, when attaching the valve to the stent during valve-stent integration, the valve itself needs to be reinforced to the stent at certain locations without hindering mechanical performance of the stent. Embodiments hereof relate to an improved balloon-expandable transcatheter valve prosthesis configured to minimize tradeoffs between the above-described competing needs.

BRIEF SUMMARY OF THE INVENTION

Embodiments hereof relate to a transcatheter valve prosthesis including a stent and a prosthetic valve. The stent has a crimped configuration for delivery within a vasculature and an expanded configuration for deployment within a native heart valve. The stent is balloon expandable. The stent includes an inflow portion formed proximate to an inflow end of the transcatheter valve prosthesis, an outflow portion formed proximate to an outflow end of the transcatheter valve prosthesis, and a transition portion extending between the inflow portion and the outflow portion. The prosthetic valve is disposed within and secured to the stent. The prosthetic valve is configured to block blood flow in one direction to regulate blood flow through a central lumen of the stent. A diameter of the inflow end of the transcatheter valve prosthesis is greater than a diameter of the outflow end of the transcatheter valve prosthesis. The stent has a tapered profile along a portion of the height thereof when in the stent is in the expanded configuration. The inflow end of the transcatheter valve prosthesis is configured to sit within and contact an aortic annulus of the native aortic valve and the outflow end of the transcatheter valve prosthesis being configured to float within an ascending aorta without substantially contacting the ascending aorta due to the tapered profile of the transcatheter valve prosthesis.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of an aortic heart valve, the invention may also be used where it is deemed useful in other valved intraluminal sites that are not in the heart. For example, the present invention may be applied to other heart valves or venous valves as well. Furthermore, there is no intention to be bound by any expressed or implied theory presented in the preceding technical field, background, brief summary or the following detailed description.

Figure 1:
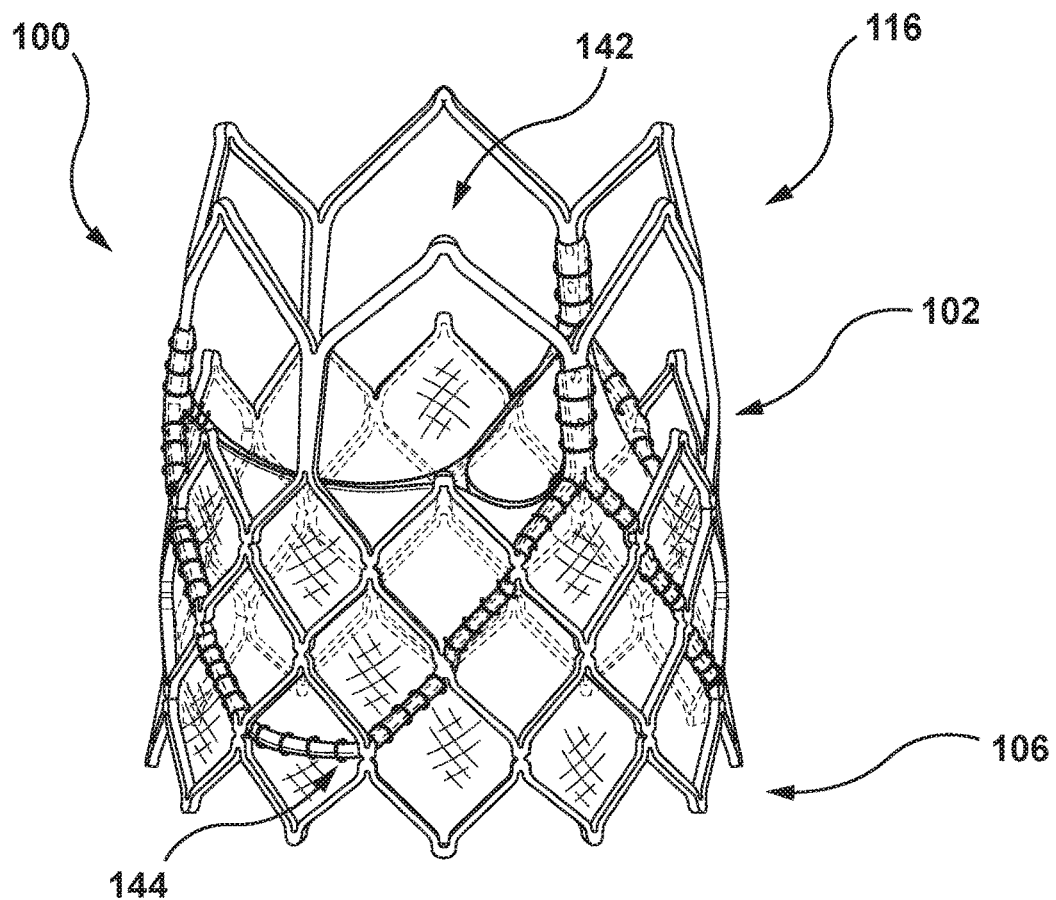
FIG. 1 is a side view of a transcatheter valve prosthesis according to an embodiment hereof, wherein a stent of the transcatheter valve prosthesis is in an expanded configuration.
Figure 2:
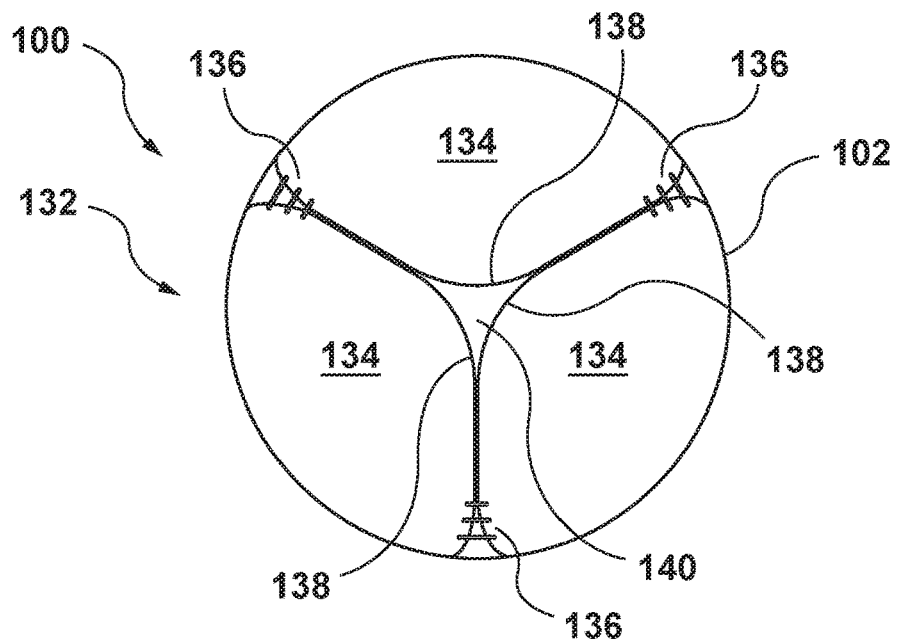
FIG. 2 is an end view illustration of the transcatheter valve prosthesis of FIG. 1.
Figure 3:
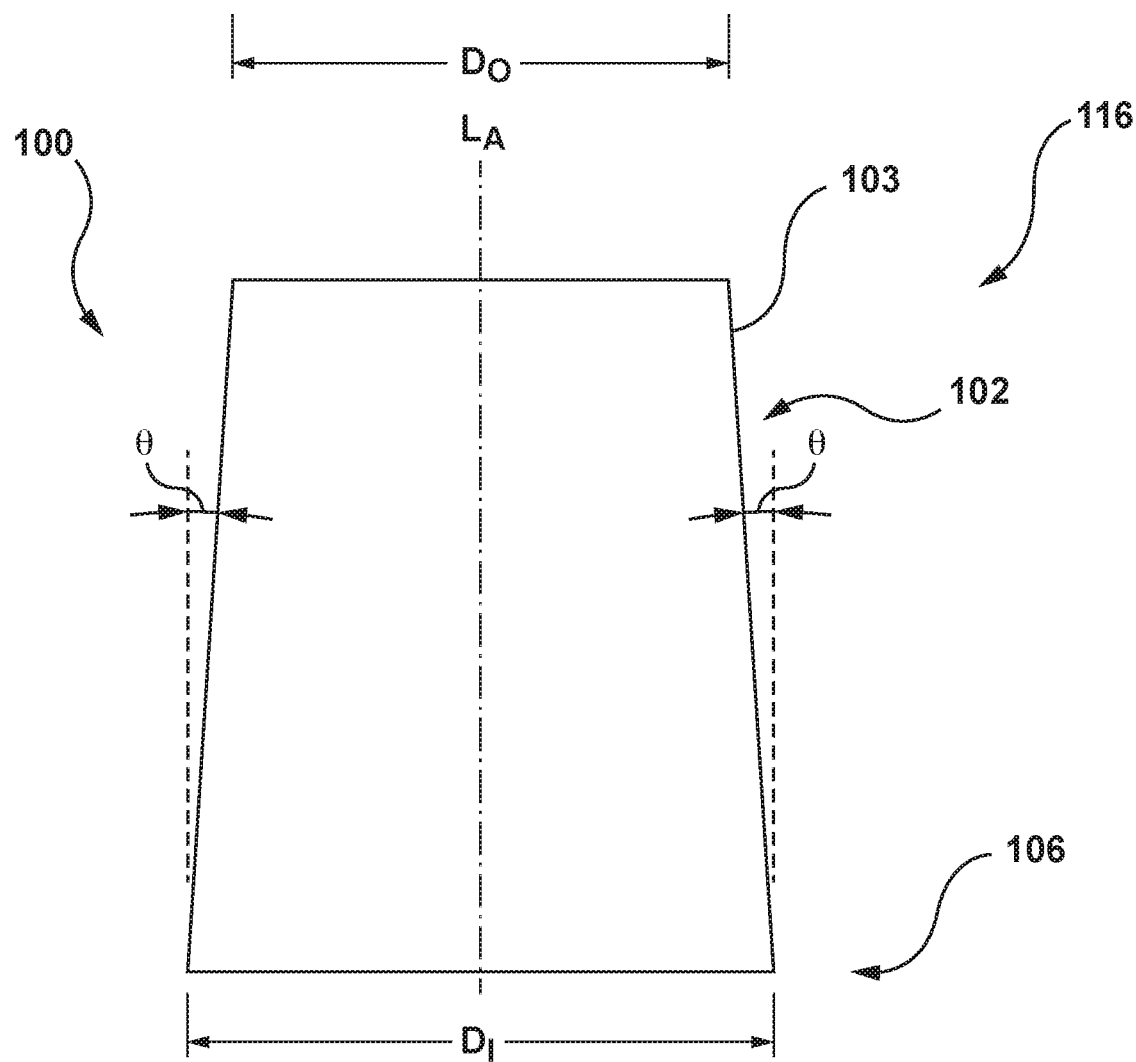
FIG. 3 is a side view illustration showing a tapered profile of the transcatheter valve prosthesis of FIG. 1, wherein the stent of the transcatheter valve prosthesis is in the expanded configuration.
Figure 4:
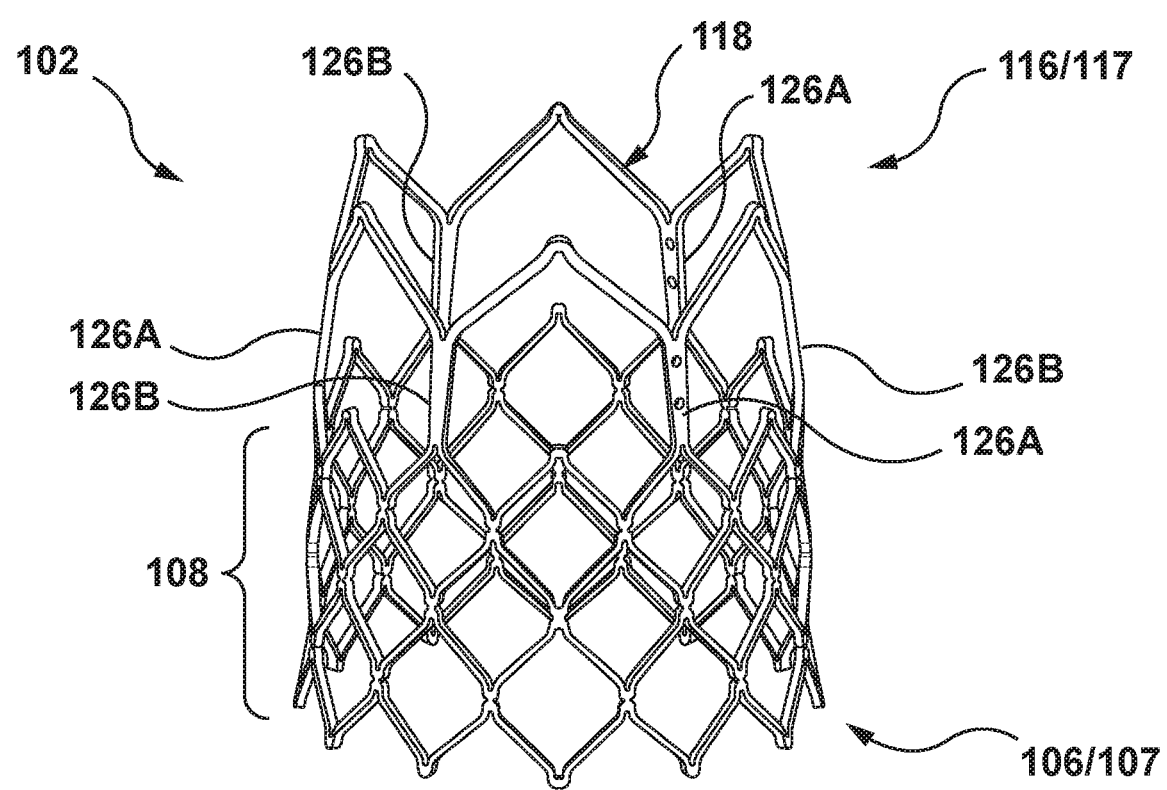
FIG. 4 is a perspective view of the stent of the transcatheter valve prosthesis of FIG. 1, wherein the stent is in the expanded configuration.
Figure 5:
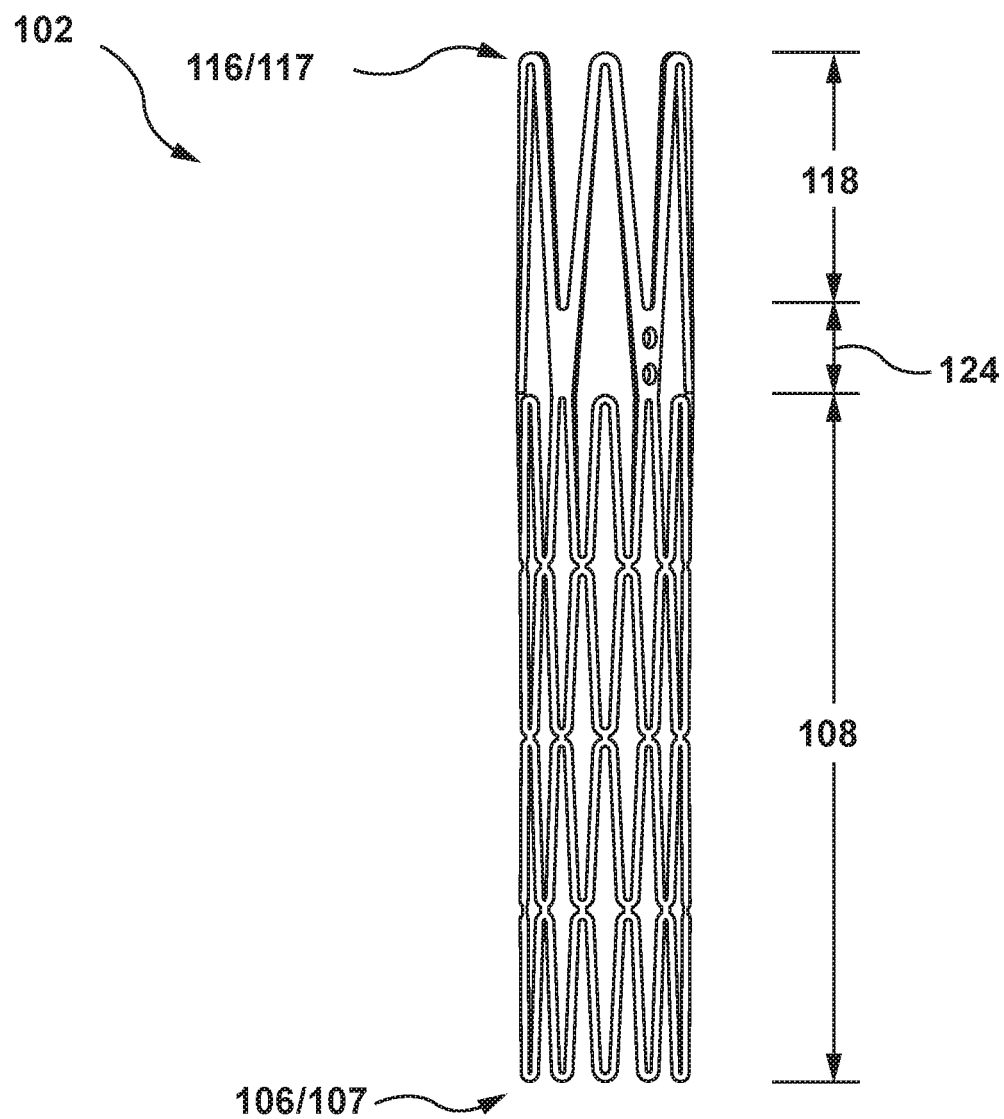
FIG. 5 is a side view of the stent of the transcatheter valve prosthesis of FIG. 1, wherein the stent is in a non-expanded or crimped configuration.

Referring to FIGS. 1-5, embodiments hereof relate to a transcatheter valve prosthesis 100 having a radially-expandable stent 102 and a prosthetic valve 132. The stent 102 is balloon expandable and has a crimped configuration for delivery within a vasculature and an expanded configuration for deployment within a native heart valve. FIG. 1 is a side view of the transcatheter valve prosthesis 100 with the stent 102 in the expanded configuration, while FIG. 2 is an end view illustration of the transcatheter valve prosthesis 100. FIG. 3 is a side view illustration showing a tapered profile of the transcatheter valve prosthesis 100. When the transcatheter valve prosthesis 100 is deployed within the valve annulus of a native heart valve, the stent 102 of the transcatheter valve prosthesis 100 is configured to be radially expanded within native valve leaflets of the patient's defective valve, to thereby retain the native valve leaflets in a permanently open state. As will be described in more detail herein, in embodiments hereof, although there can be some incidental, unintended contact between the ascending aorta and valve prosthesis 100, the transcatheter valve prosthesis 100 is configured for replacement for an aortic valve such that an inflow end 106 of the transcatheter valve prosthesis 100 is configured to sit within and contact an aortic annulus of the native aortic valve and an outflow end 116 of the transcatheter valve prosthesis 100 is configured to float within an ascending aorta without contacting or without substantially contacting the walls of the ascending aorta due to a tapered profile of the transcatheter valve prosthesis 100.

The stent 102 of the transcatheter valve prosthesis 100 is a frame or scaffold that supports the prosthetic valve 132 including one or more valve leaflets 134 within the interior of the stent 102. The prosthetic valve 132 is capable of blocking flow in one direction to regulate flow there-through via the valve leaflets 134 that may form a bicuspid or tricuspid replacement valve. FIG. 2 is an end view of FIG. 1 taken from the outflow end 116 of the transcatheter valve prosthesis 100 and illustrates an exemplary tricuspid valve having three valve leaflets 134, although a bicuspid leaflet configuration may alternatively be used in embodiments hereof. More particularly, as the transcatheter valve prosthesis 100 is configured for placement within a native aortic valve having three leaflets, the prosthetic valve 132 may include three valve leaflets 134. However, the transcatheter valve prosthesis 100 is not required to have the same number of leaflets as the native valve. If the transcatheter valve prosthesis 100 is alternatively configured for placement within a native valve having two leaflets such as the mitral valve, the prosthetic valve 132 may include two or three valve leaflets. The valve leaflets 134 may be attached to a graft material 144 which encloses or lines a portion of the stent 102 as would be known to one of ordinary skill in the art of prosthetic tissue valve construction. The valve leaflets 134 are sutured or otherwise securely and sealingly attached along their bases to the interior surface of the graft material 144, or otherwise attached to the stent 102. Adjoining pairs of leaflets are attached to one another at their lateral ends to form commissures 136, with free edges 138 of the valve leaflets 134 forming coaptation edges that meet in area of coaptation 140.

The valve leaflets 134 may be made of pericardial material; however, the valve leaflets 134 may instead be made of another material. Natural tissue for the valve leaflets 134 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as the valve leaflets 134 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 144 may enclose or line the stent 102 as would be known to one of ordinary skill in the art of prosthetic tissue valve construction. Graft material 144 may be a natural or biological material such as pericardium or another membranous tissue such as intestinal submucosa. Alternatively, graft material 144 may be a low-porosity woven fabric, such as polyester, Dacron fabric, or PTFE, which creates a one-way fluid passage when attached to the stent. In one embodiment, graft material 144 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

As previously stated, the stent 102 is balloon-expandable as would be understood by one of ordinary skill in the art. As such, the stent 102 is made from a plastically deformable material such that when expanded by a dilatation balloon, the stent 102 maintains its radially expanded configuration. The stent 102 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The stent 102 is configured to be rigid such that it does not deflect or move when subjected to in-vivo forces, or such that deflection or movement is minimized when subjected to in-vivo forces. In an embodiment, the radial stiffness (i.e., a measurement of how much the stent 102 deflects when subjected to in-vivo forces) of the stent 102 is between 80 N/m and 120 N/m, and the radial stiffness of the stent 102 scaled across the deployed height thereof is approximately 5 N/mm². In an embodiment, the radial stiffness of the stent 102 is greater than 100 N/m. Further, in an embodiment, the device recoil (i.e., a measurement of how much the stent 102 relaxes after balloon deployment) is below 15% and the approximately recoil after deployment is between 1 mm and 2 mm. Further, in an embodiment, the device crush or yield (i.e., the radial force at which the stent 102 yields) is approximately 200 N.

FIG. 3 is a side view schematic illustration showing a tapered profile of the transcatheter valve prosthesis 100 when the stent 102 is in the expanded configuration. When expanded, an inflow diameter $D_I$ of the inflow end 106 of the transcatheter valve prosthesis 100 is the greater than an outflow diameter $D_O$ of the outflow end 116 of the transcatheter valve prosthesis 100. In an embodiment, the inflow diameter $D_I$ may range between 20 and 32 mm and the outflow diameter $D_O$ may range between 16 and 28 mm in order to accommodate dimensions of the native valve anatomy. Stated another way, it may be desirable for the transcatheter valve prosthesis 100 to be available in varying size increments to accommodate varying diameters or sizes of a patient's native annulus. The transcatheter valve prosthesis 100 has a tapered profile along at least a portion of the height thereof when the stent 102 is in the expanded configuration. In an embodiment, the transcatheter valve prosthesis 100 has a tapered profile along the entire height thereof when the stent 102 is in the expanded configuration. Stated another way, an outer surface 103 of the stent 102 is angled or tapered relative to a longitudinal axis LA of the transcatheter valve prosthesis 100. More particularly, when the stent 102 is in the expanded configuration, the outer surface 103 of the stent 102 forms an acute angle Θ with respect to a plane extending parallel to the longitudinal axis LA of the transcatheter valve prosthesis 100 as shown in FIG. 3. In an embodiment, the acute angle Θ ranges between 2 and 35 degrees. In an embodiment, the acute angle Θ is 3 degrees. The tapered profile of the transcatheter valve prosthesis 100 extends at the same acute angle Θ for the entire height of the stent 102 between the outflow and inflow ends 116, 106 of the transcatheter valve prosthesis 100. The value of the acute angle Θ depends upon patient specific needs and anatomy. In addition, the value of the acute angle Θ balances the competing interests that the outflow end 116 of the transcatheter valve prosthesis 100 does not touch or contact the native anatomy, while further ensuring that the outflow diameter $D_O$ of the outflow end 116 is of a sufficient size to ensure valve performance and avoid aortic stenosis.

As previously stated, the transcatheter valve prosthesis 100 is configured for replacement for an aortic valve such that the inflow end 106 of the transcatheter valve prosthesis 100 is configured to sit within and contact an aortic annulus of the native aortic valve and the outflow end 116 of the transcatheter valve prosthesis 100 is configured to float freely within the outflow track without contacting or without substantially contacting the walls of the ascending aorta due to the tapered profile of the transcatheter valve prosthesis 100. More particularly, due to the tapered profile, the outflow end 116 of the transcatheter valve prosthesis 100 does not interact with or touch the surrounding anatomy, i.e., the walls of the ascending aorta. Further, the tapered profile of the transcatheter valve prosthesis 100 prevents valve interaction with the anatomy of the aortic valve, particularly the sino tubular junction anatomy. As will be described in more detail herein with respect to FIGS. 11 and 12, the tapered profile further permits alternative access routes to the coronary arteries. After implantation in situ, due to the tapered profile of the transcatheter valve prosthesis 100, there is sufficient space between the outer surface 103 of the stent and the ascending aorta to be crossed with a coronary guide catheter into either the right coronary artery or the left main coronary artery.

The transcatheter valve prosthesis 100 is configured for supra annular placement within a native aortic valve such that the prosthetic valve 132 sits superior to or downstream of the native leaflets of the native aortic valve when implanted in situ. A height or length of the stent 102 in the expanded configuration is between 22 and 33 mm, the height being measured from the most proximal part thereof (endmost inflow crowns 110A, which will be described in more detail herein) to the most distal part thereof (endmost outflow crowns 120A, which will be described in more detail herein). Stated another way, the height of the stent 102 in the expanded configuration is measured from a proximal end of the stent to a distal end of the stent. In an embodiment hereof, a height or length of the stent 102 in the expanded configuration is approximately 30 mm. The height or length of the stent 102 may vary from that depicted herein in order to accommodate dimensions of the native valve anatomy. In another embodiment hereof, the transcatheter valve prosthesis 100 is configured for intra annular placement within a native aortic valve such that the prosthetic valve 132 sits within the native leaflets of the native aortic valve when implanted in situ.

Figure 6:
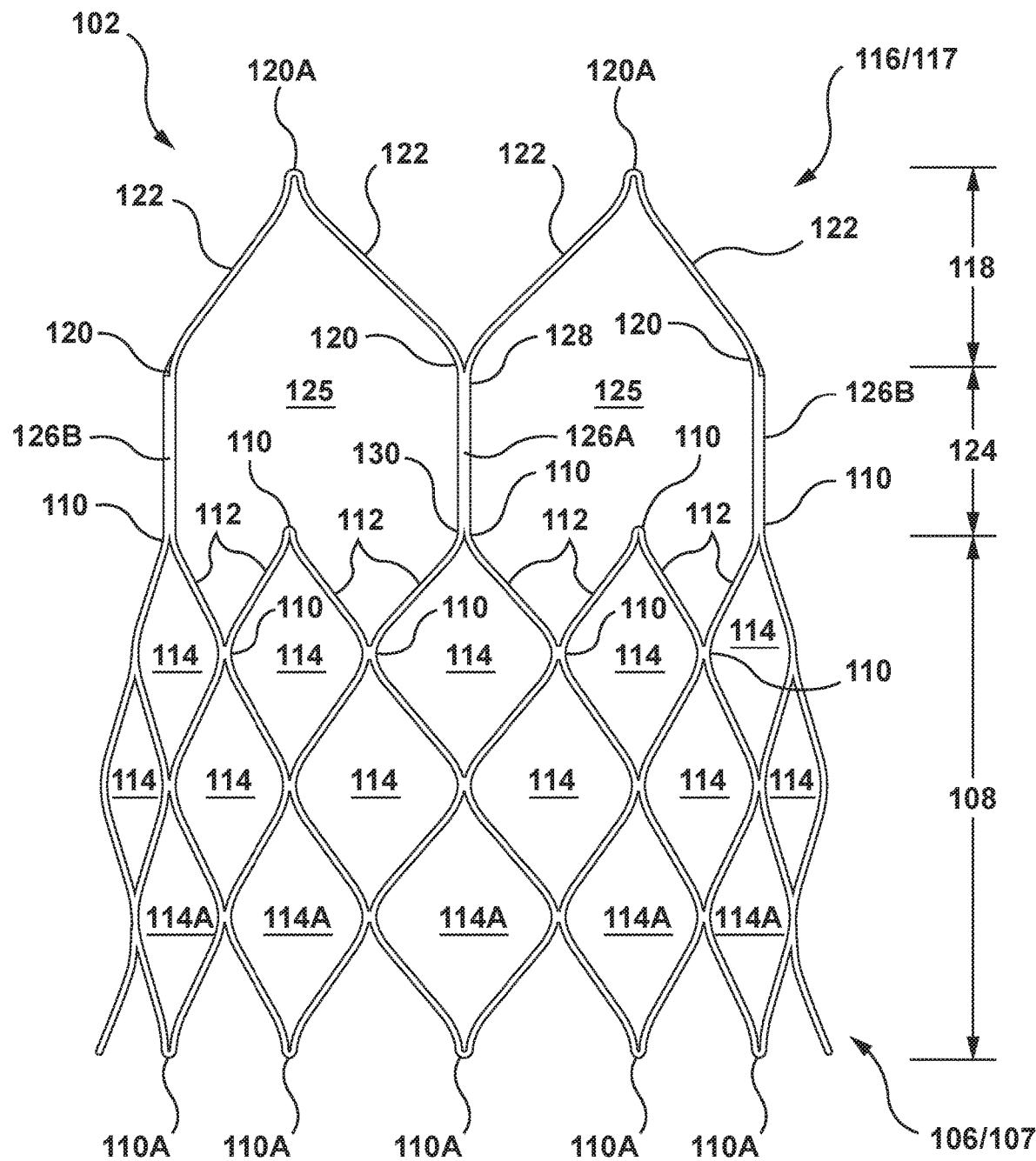
FIG. 6 is a side view of the stent of the transcatheter valve prosthesis of FIG. 1, wherein the stent is in the expanded configuration.

The stent 102 will now be described in more detail. The stent 102 includes an inflow portion 108, an outflow portion 118, and a transition portion 124 bridging, connecting, or otherwise extending between the inflow portion 108 and the outflow portion 118. The stent 102 is a generally tubular component defining a central lumen or passageway 142, and includes an inflow or proximal end 107 that defines the inflow or proximal end 106 of the transcatheter valve prosthesis and an outflow or distal end 117 that defines the outflow or distal end 116 of the transcatheter valve prosthesis 100. The stent 102 may be formed by a laser-cut manufacturing method and/or another conventional stent forming method as would be understood by one of ordinary skill in the art. The cross-section of the stent 102 may be circular, ellipsoidal, rectangular, hexagonal, square, or other polygonal shape, although at present it is believed that circular or ellipsoidal may be preferable with the transcatheter valve prosthesis 100 being provided for replacement of an aortic valve. The stent 102 has an expanded configuration, which is shown in the perspective and side views of FIGS. 4 and 6, respectively, and a non-expanded or crimped configuration, which is shown in the side view of FIG. 5. Non-expanded or crimped configuration as used herein refers to the configuration of the stent 102 after crimping onto a balloon of a balloon catheter for delivery.

Figure 6A:
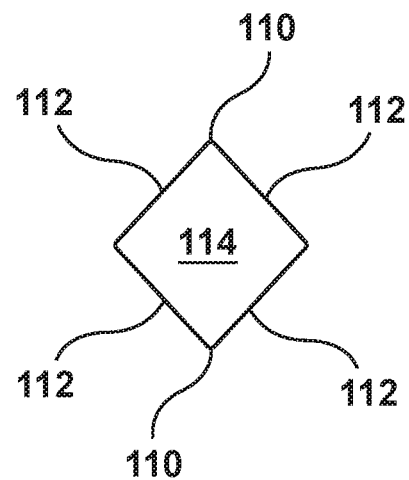
FIG. 6A is an enlarged side view of a single cell or side opening of an inflow portion of the stent of the transcatheter valve prosthesis of FIG. 1, wherein the stent is in the expanded configuration.
Figure 7:
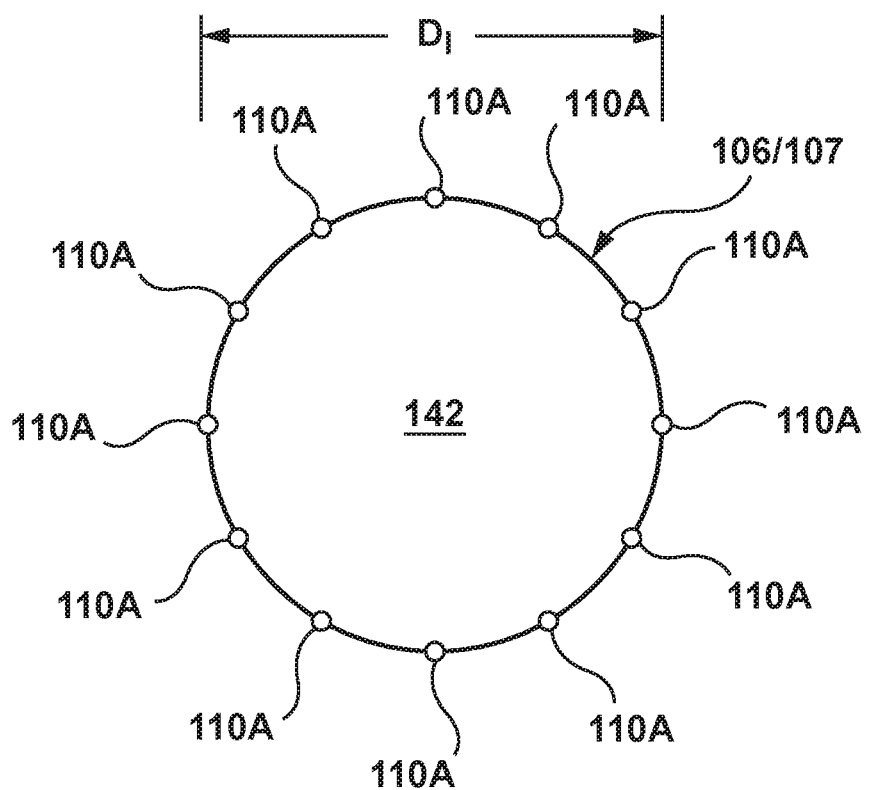
FIG. 7 is an end view of an inflow end of the transcatheter valve prosthesis of FIG. 1.

The inflow portion 108 of the stent 102 is formed proximate to the inflow end 107 of the stent 102. The inflow portion 108 includes a plurality of crowns 110 and a plurality of struts 112 with each crown 110 being formed between a pair of opposing struts 112. Each crown 110 is a curved segment or bend extending between opposing struts 112. The inflow portion 108 is generally tubular, with a plurality of cells or side openings 114 being defined by the plurality of crowns 110 and the plurality of struts 112. In an embodiment, the plurality of side openings 114 may be diamond-shaped. More particularly, as best shown in FIG. 6A which is a side view of a single side opening 114 of the inflow portion 108 of the stent 102, each side opening 114 is formed by two pairs of opposing crowns 110 and four struts 112 therebetween. Each side opening 114 is symmetrical for easier integration with the prosthetic valve 132. A series of endmost inflow side openings 114A and a series of endmost inflow crowns 110A are formed at the inflow end 106 of the transcatheter valve prosthesis 100. The inflow end 106 of transcatheter valve prosthesis 100 has a total of twelve endmost inflow crowns 110A, as best shown in FIG. 7 which is an end view of the inflow end 106 of the transcatheter valve prosthesis 100.

Figure 8:
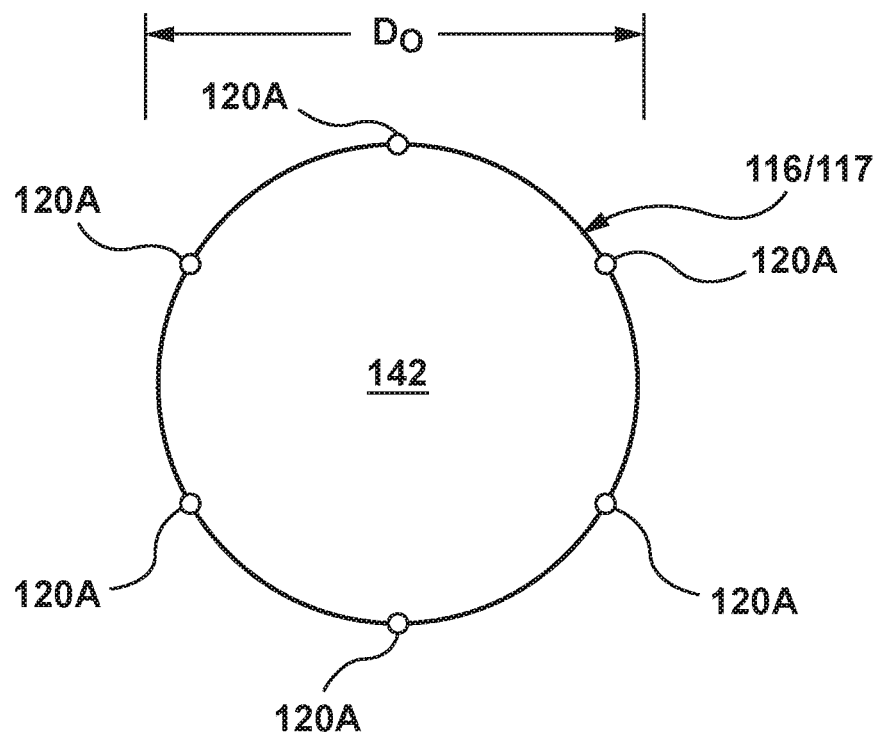
FIG. 8 is an end view of an outflow end of the transcatheter valve prosthesis of FIG. 1.

The outflow portion 118 of the stent 102 is formed proximate to the outflow end 117 of the stent 102. The outflow portion 118 includes a plurality of crowns 120 and a plurality of struts 122 with each crown 120 being formed between a pair of opposing struts 122. Each crown 120 is a curved segment or bend extending between opposing struts 122. The outflow portion 118 is a ring. A series of endmost outflow crowns 120A are formed at the outflow end 117 of the stent 102. The outflow end 117 has a total of six endmost outflow crowns 120A, as best shown in FIG. 8 which is an end view of the outflow end 116 of the transcatheter valve prosthesis 100.

The transition portion 124 bridges, connects, or otherwise extends between the inflow portion 108 and the outflow portion 118. The transition portion 124 includes a total of six axial frame members 126, each axial frame member 126 extending between a crown 120 of the outflow portion 118 and a crown 110 of the inflow portion 108. More particularly, each axial frame member 126 is an axial segment having a first end 128 connected to a crown 120 of the outflow portion 118 and a second end 130 connected to a crown 110 of the inflow portion 108. The axial frame members 126 are substantially parallel to the central longitudinal axis of the stent 102 taking into account the angle of the taper, described below. Each axial frame member 126 is disposed approximately halfway between a pair of adjacent endmost outflow crowns 120A. Three of the six axial frame members 126 are commissure posts 126A and aligned with and attached to a respective commissure of the three leaflets 134 of the prosthetic valve 132. Three of the axial frame members 126 are axial struts 126B and each is disposed between adjacent commissure posts 126A. In this embodiment, the endmost outflow crowns 120A of are not connected to axial frame members 126 of the transition portion 124 but rather may be considered to be free or unattached while the remaining outflow crowns 120 of the outflow portion 118 are connected to the axial frame members 126 and disposed closer to the inflow end 106 than the endmost outflow crowns 120A. The axial frame members 126 aid in valve alignment and coaptation. More particularly, since commissure posts 126A are used as connection locations for the commissures of the three leaflets 134 of the prosthetic valve 132, the commissure posts 126A shape the leaflets 134 and reinforce, strength, or otherwise support the leaflets 134 during opening and closing thereof, thereby providing more reliable leaflet alignment and coaptation. In addition, the axial frame members 126 minimize the crossing profile of the transcatheter valve prosthesis 100 since the axial frame members 126 are circumferentially spaced apart from each other while maximizing symmetrical cell expansion of the stent 102 since the axial frame members 126 are spaced at generally the same distance from each other around the periphery of the stent 102. Symmetrical cell expansion ensures that the stent 102 crimps well onto a balloon of a balloon catheter for delivery. Poor crimp quality may lead to portions of the stent overlapping when crimped, which in turn may cause tissue damage to the valve leaflets of the prosthetic valve during the crimping process.

The prosthetic valve 132 is disposed within and secured to at least the transition portion 124 of the stent 102 at the commissure posts 126A. In addition, the prosthetic valve 132 may also be disposed within and secured to the inflow portion 108 of the stent 102 and/or the outflow portion 116 of the stent 102.

Figure 6B:
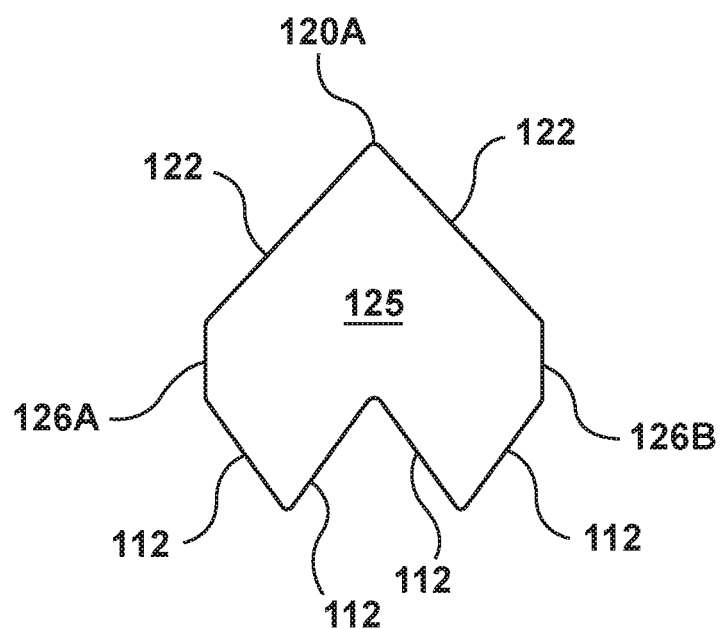
FIG. 6B is an enlarged side view of a single endmost cell or side opening of the stent of the transcatheter valve prosthesis of FIG. 1, wherein the stent is in the expanded configuration.

In the embodiment shown, there is a single row of struts 122 and crowns 120 between the first ends 128 of the axial frame members 126 and the outflow end 117 of the stent 102. Further, in the embodiment shown, exactly two struts 122 and a single crown 120 of the outflow portion 118 are disposed between circumferentially adjacent axial frame members 126. Such an arrangement provides a series of six endmost outflow cells or side openings 125 formed at the outflow portion 118 of the stent 102. Each endmost outflow side opening 125 is generally heart-shaped. More particularly, as best shown in FIG. 6B, which is a side view of a single endmost outflow side opening 125 of the stent 102, each endmost outflow side opening 125 is defined by two adjacent struts 122 of the outflow portion 118, four adjacent struts 112 of the inflow portion 108, and two adjacent axial frame members 126 of the transition portion 124. The endmost outflow side openings 125 of the outflow portion 118 are relatively larger than the plurality of side openings 114 of the inflow portion 108 (defined by four adjacent struts 112 of the inflow portion 108) to improve access to the coronary arteries. More particularly, the endmost outflow side openings 125 of the outflow portion 118 are configured to be of sufficient size to be crossed with a coronary guide catheter into either the right coronary artery or the left main coronary artery once the transcatheter valve prosthesis 100 is deployed in situ.

Also in the embodiment shown, the inflow portion 108 includes exactly four rows of struts 112 and crowns 110 between the second ends 130 of the axial frame members 126 and the inflow end 107 of the stent 102. Further, four struts 112 and three crowns 110 of the inflow portion are disposed between the second ends 130 of circumferentially adjacent axial frame members 126.

Figure 9:
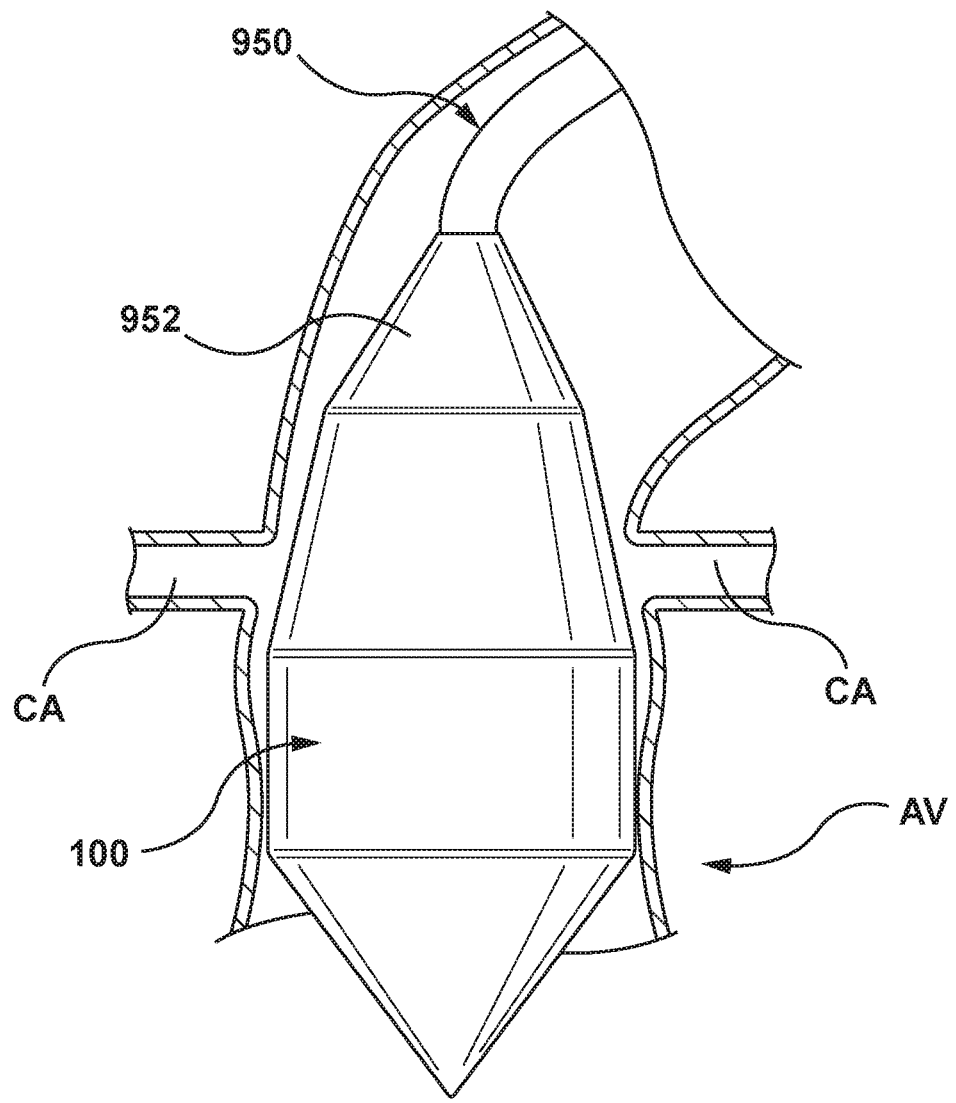
FIG. 9 is a schematic view illustration of the transcatheter valve prosthesis of FIG. 1 during implantation within a native aortic valve annulus with a balloon catheter, wherein a balloon of the balloon catheter is tapered.

FIG. 9 is a schematic view illustration of the transcatheter valve prosthesis 100 during implantation within a target diseased native aortic valve AV with a balloon catheter 950. FIG. 9 also illustrates placement of the coronary arteries CA. A balloon 952 of the balloon catheter 950 has a tapered profile when inflated, as shown in FIG. 9. The tapered profile of the balloon 952 corresponds or matches the tapered profile of the transcatheter valve prosthesis 100. Delivery of the transcatheter valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. The transcatheter valve prosthesis 100 has a crossing profile of between 10-26 Fr, the crossing profile being defined as the outside diameter (OD) of the transcatheter valve prosthesis 100 after it is crimped onto the balloon and allowed to recoil from the crimping action. During delivery, the transcatheter valve prosthesis 100 remains compressed until it reaches a target diseased native aortic valve AV, at which time the balloon 952 of the balloon catheter 950 is inflated in order to radially expand the transcatheter valve prosthesis 100 in situ. The balloon catheter 950 is then removed and the transcatheter valve prosthesis 100 remains deployed within the target native aortic valve AV.

Figure 10:
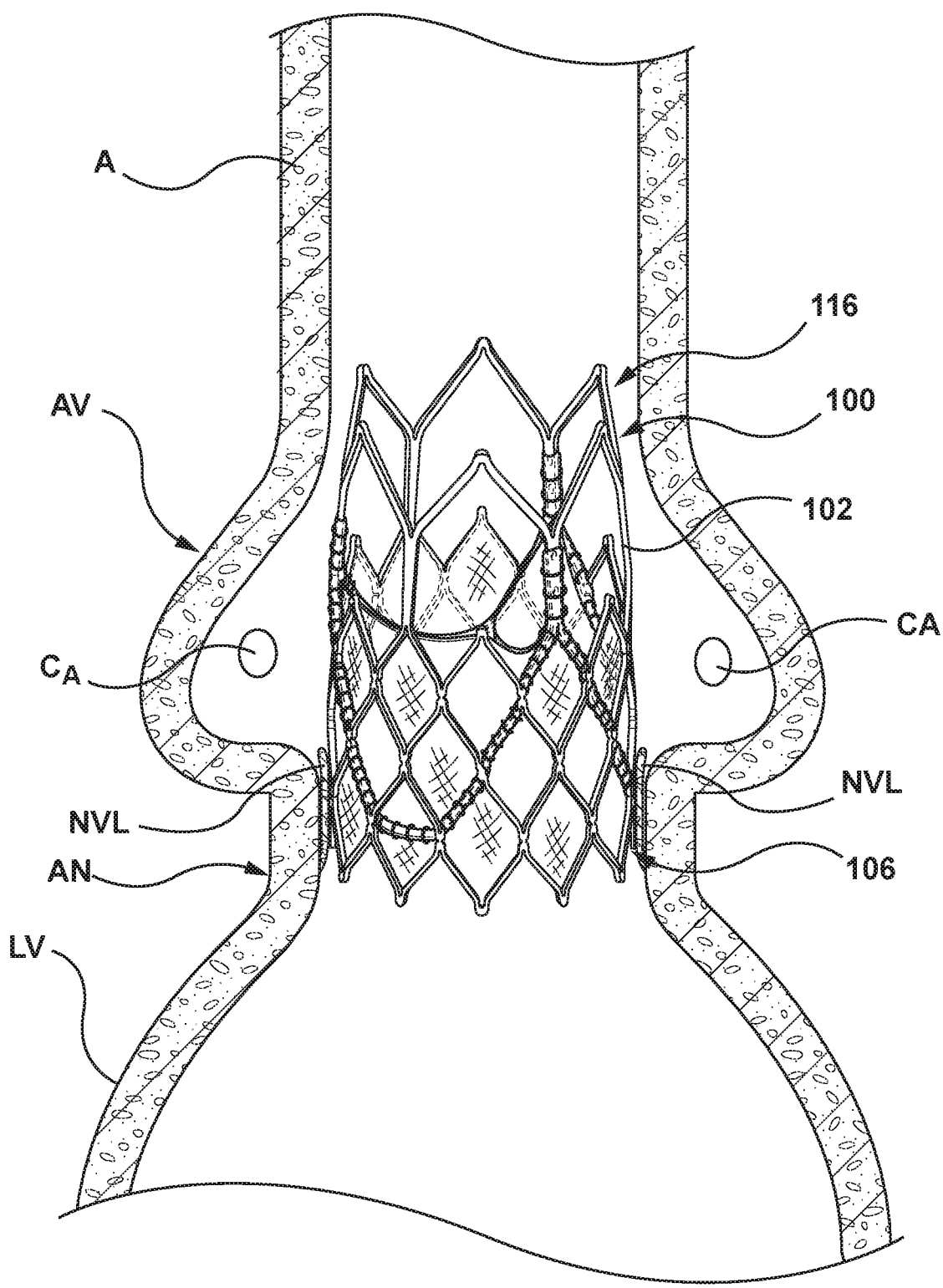
FIG. 10 is a side view illustration of the transcatheter valve prosthesis of FIG. 1 implanted within a native aortic valve annulus.

FIG. 10 illustrates the transcatheter valve prosthesis 100 implanted in situ within a target diseased native aortic valve AV that extends between a patient's left ventricle LV and a patient's aorta A. FIG. 10 also illustrates placement of the coronary arteries CA. As previously described herein, the transcatheter valve prosthesis 100 is configured for supra annular placement within the native aortic valve AV such that the prosthetic valve 132 (not shown in FIG. 10) sits superior to or downstream the native valve leaflets NVL of the native aortic valve AV when implanted in situ. When the transcatheter valve prosthesis 100 is deployed within the valve annulus of a native heart valve, the stent 102 is configured to be expanded within native valve leaflets of the patient's defective valve, to thereby retain the native valve leaflets in a permanently open state. As shown on FIG. 10, the transcatheter valve prosthesis 100 is implanted in situ such that the inflow end 106 of the transcatheter valve prosthesis 100 sits within and contacts an aortic annulus AN of the native aortic valve AV and the outflow end 116 of the transcatheter valve prosthesis 100 floats freely within the outflow track without contacting or without substantially contacting the walls of the ascending aorta A due to the tapered profile of the transcatheter valve prosthesis 100. The outflow end 116 of the transcatheter valve prosthesis 100 does not interact with or touch the surrounding anatomy, i.e., the ascending aorta A, and the tapered profile of the transcatheter valve prosthesis 100 prevents valve interaction with the anatomy of the aortic valve, particularly the sino tubular junction anatomy.

Figure 11:
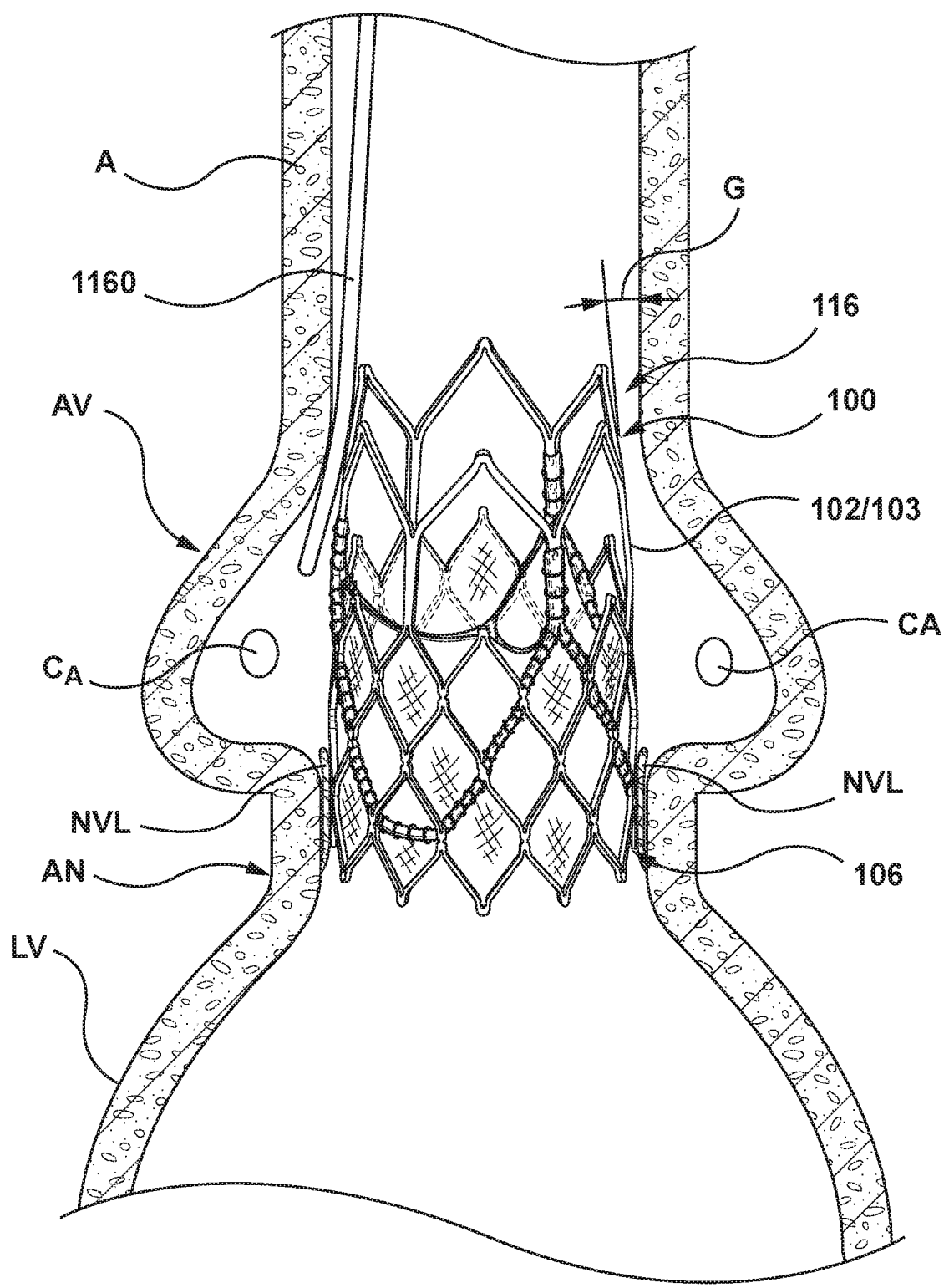
FIG. 11 is a schematic view illustration of the transcatheter valve prosthesis of FIG. 1 after implantation within a native aortic valve annulus, wherein a coronary guide catheter is being delivered to a coronary artery within a space between the native anatomy and an outermost surface of the transcatheter valve prosthesis of FIG. 1.
Figure 12:
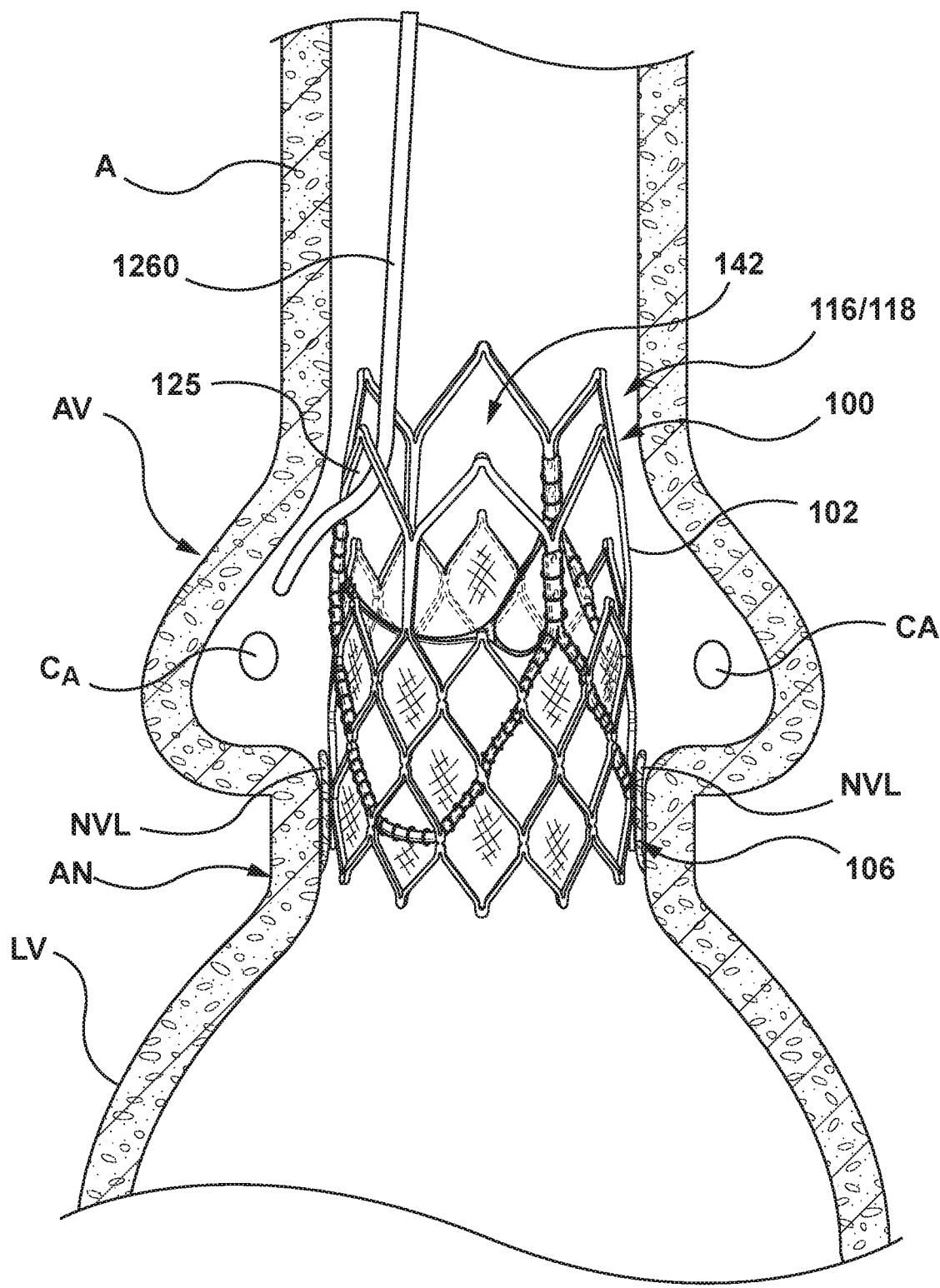
FIG. 12 is a schematic view illustration of the transcatheter valve prosthesis of FIG. 1 after implantation within a native aortic valve annulus according to another embodiment hereof, wherein a coronary guide catheter is being delivered to a coronary artery through an endmost outflow side opening of the transcatheter valve prosthesis of FIG. 1.

Following implantation of the transcatheter valve prosthesis 100, it may be desirable to access a coronary artery CA. As shown in FIG. 11 and FIG. 12, due to the configuration of the transcatheter valve prosthesis 100, a physician may transluminally access a coronary artery CA in one of two ways. In FIG. 11, a coronary artery CA is accessed via a space between the native anatomy and the outer surface 103 of the stent 102 while in FIG. 12, a coronary artery CA is accessed via one of the endmost outflow side openings 125 of the stent 102.

More particularly, FIG. 11 is a schematic view illustration of the transcatheter valve prosthesis 100 after implantation within a target diseased native aortic valve AV that extends between a patient's left ventricle LV and a patient's aorta A. In FIG. 11, a coronary guide catheter 1160 is disposed within an opening or gap G between the native anatomy and the outer surface 103 of the stent 102. More particularly, due to the tapered profile of the transcatheter valve prosthesis 100 and the fact that the outflow end 116 of the transcatheter valve prosthesis 100 floats freely within the outflow track without contacting or without substantially contacting the ascending aorta A, there is sufficient space or room for the coronary guide catheter 1160 to cross or be delivered to a coronary artery CA within the gap G defined between the outer surface 103 of the stent 102 and the ascending aorta.

FIG. 12 is a schematic view illustration of the transcatheter valve prosthesis 100 after implantation within a target diseased native aortic valve AV that extends between a patient's left ventricle LV and a patient's aorta A. In FIG. 12, a coronary guide catheter 1260 is disposed within the central lumen 142 of the stent 102 and traverses the stent 102 through one of the endmost outflow side openings 125 of the stent 102. As described above, the endmost outflow side openings 125 of the outflow portion 118 are configured to be of sufficient size to be easily crossed with a coronary guide catheter into either the right coronary artery or the left main coronary artery once the transcatheter valve prosthesis 100 is deployed in situ. A physician thus has multiple options for transluminally accessing the coronary arteries due to the tapered profile of the transcatheter valve prosthesis 100 and the size of the endmost outflow side openings 125.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
a stent having a crimped configuration for delivery within a vasculature and an expanded configuration for deployment within a native aortic valve, wherein the stent is balloon expandable and sufficiently rigid such that the stent does not deflect when subjected to in-vivo forces, the stent having an inflow portion formed proximate to an inflow end of the transcatheter valve prosthesis, an outflow portion formed proximate to an outflow end of the transcatheter valve prosthesis, and a transition portion extending between the inflow portion and the outflow portion; and
a prosthetic valve disposed within and secured to the stent, the prosthetic valve being configured to block blood flow in one direction to regulate blood flow through a central lumen of the stent,
wherein an inflow diameter of an inflow end of the stent is greater than an outflow diameter of an outflow end of the stent and the stent has a tapered profile along an entire height thereof when the stent is in the expanded configuration and subjected to in-vivo forces, such that an outermost surface of the transcatheter valve prosthesis also has a tapered profile along an entire height thereof, wherein the entire height of the stent in the expanded configuration is configured to extend from an aortic annulus of the native aortic valve to an ascending aorta such that the stent extends beyond a sino tubular junction disposed between the aortic annulus and the ascending aorta, and wherein the inflow end of the transcatheter valve prosthesis is configured to sit within and contact the aortic annulus of the native aortic valve and the outflow end of the transcatheter valve prosthesis is configured to float within the ascending aorta without contacting the ascending aorta due to the tapered profile of the stent, and wherein the tapered profile of the stent prevents interaction between the transcatheter valve prosthesis and the sino tubular junction, and wherein the transcatheter valve prosthesis is configured for supra annular placement within the native aortic valve such that the prosthetic valve sits superior to the native leaflets of the native aortic valve when implanted in situ, and wherein the tapered profile of the stent forms an acute angle relative to a longitudinal axis of the transcatheter valve prosthesis along the entire height of the stent between the inflow end and the outflow end of the transcatheter valve prosthesis.

2. The transcatheter valve prosthesis of claim 1, wherein the acute angle is between 2 and 35 degrees.

3. The transcatheter valve prosthesis of claim 1, wherein the prosthetic valve includes three leaflets and three commissures, each commissure being formed by attached adjacent lateral ends of an adjoining pair of the three leaflets.

4. The transcatheter valve prosthesis of claim 1, the inflow portion including a plurality of crowns and a plurality of struts with each crown being formed between a pair of opposing struts, a plurality of side openings being defined by the plurality of crowns and the plurality of struts, wherein endmost inflow side openings and endmost inflow crowns are formed at the inflow end of the stent.

5. The transcatheter valve prosthesis of claim 4, wherein the inflow end of the stent has a total of twelve endmost inflow crowns.

6. The transcatheter valve prosthesis of claim 5, wherein the outflow portion includes a plurality of crowns and a plurality of struts with each crown being formed between a pair of opposing struts, wherein endmost outflow crowns are formed at the outflow end of the stent.

7. The transcatheter valve prosthesis of claim 6, wherein the outflow end of the stent has a total of six endmost outflow crowns and the transition portion includes a total of six axial frame members.

8. The transcatheter valve prosthesis of claim 7, wherein the transition portion includes a total of six endmost outflow side openings formed at the outflow end of the stent, each endmost outflow side opening being defined by two struts of the outflow portion, four struts of the inflow portion, and two axial frame members of the transition portion.

9. The transcatheter valve prosthesis of claim 8, wherein the inflow portion includes at least four rows of struts and crowns formed between adjacent pairs of said struts, wherein the at least four rows of struts and crowns of the inflow portion are formed between the inflow end of the axial frame members and an inflow end of the stent.

10. The transcatheter valve prosthesis of claim 9, wherein the outflow portion includes a single row of struts and crowns formed between adjacent pair of said struts, the outflow portion being coupled to outflow ends of the axial frame members.

11. The transcatheter valve prosthesis of claim 10, wherein exactly two struts of the plurality of struts of the outflow portion are disposed between circumferentially adjacent axial frame members.

12. The transcatheter valve prosthesis of claim 1,
wherein the transition portion includes exactly six axial frame members, and
wherein three of the six axial frame members are commissure posts and three of the six axial frame members are axial struts, and
wherein each of the axial struts is disposed between circumferentially adjacent commissure posts such that the axial struts and the commissure posts alternate around the circumference of the stent.

13. The transcatheter valve prosthesis of claim 12, wherein the prosthetic valve includes three leaflets and three commissures, and each commissure of the leaflets is coupled to a corresponding commissure post of the stent.

14. The transcatheter valve prosthesis of claim 1,
wherein the transition portion includes a plurality of axial frame members and the inflow portion includes at least four rows of struts and crowns formed between adjacent pairs of said struts, wherein the at least four rows of struts and crowns of the inflow portion are formed between an inflow end of the axial frame members and the inflow end of the stent, and wherein one of the at least four rows of struts and crowns of the inflow portion includes crowns coupled to the inflow ends of the axial frame members, and wherein the one row of the at least four rows of struts and crowns includes at least four struts between circumferentially adjacent axial frame members.

15. The transcatheter valve prosthesis of claim 14, wherein the one row includes exactly four struts between circumferentially adjacent axial frame members.

16. The transcatheter valve prosthesis of claim 1, wherein the transition portion includes a plurality of axial frame members and the inflow portion includes exactly four rows of struts and crowns formed between adjacent pairs of said struts, wherein the four rows of struts and crowns of the inflow portion are formed between an inflow end of the axial frame members and the inflow end of the stent.

17. The transcatheter valve prosthesis of claim 1,
wherein the transition portion includes a plurality of axial frame members, and
wherein the plurality of axial frame members includes a plurality of axial struts and a plurality of commissure posts, wherein there are the same number of axial struts and commissure posts, wherein each of the axial struts is disposed between circumferentially adjacent commissure posts.

18. The transcatheter valve prosthesis of claim 1, wherein the entire height of the stent in the expanded configuration is approximately 30 mm.

* * * * *